United States Patent [19]
Tano et al.

[11] Patent Number: 5,921,998
[45] Date of Patent: Jul. 13, 1999

[54] MEMBRANE ERASER

[75] Inventors: Yasuo Tano, Kobe; Motohiro Kamei, Osaka; Masato Ooji, Minoo; Yoshihiro Saitou, Takarazuka, all of Japan; Park In Won, Seoul, Rep. of Korea; John M. Lewis, Birmingham, Mich.

[73] Assignee: Inami & Co., Ltd., Tokyo, Japan

[21] Appl. No.: 09/058,183

[22] Filed: Apr. 10, 1998

Related U.S. Application Data

[51] Int. Cl.⁶ .................................................. A61B 17/24
[52] U.S. Cl. ........................................... 606/161; 606/162
[58] Field of Search ................................ 606/161, 1, 162, 606/131

[56] References Cited

U.S. PATENT DOCUMENTS

| | | | |
|---|---|---|---|
| 3,809,101 | 5/1974 | Shimizu | 132/76.4 |
| 4,285,072 | 8/1981 | Morcher et al. | 3/13 |
| 4,909,784 | 3/1990 | Dubroff | 604/49 |
| 5,437,754 | 8/1995 | Calhoun | 156/231 |
| 5,735,793 | 4/1998 | Takahashi et al. | 606/153 |

*Primary Examiner*—Michael Buiz
*Assistant Examiner*—Vy Qi Bui
*Attorney, Agent, or Firm*—Oblon, Spivak, McClelland, Maier & Neustadt, P.C.

[57] ABSTRACT

An instrument for removing proliferative membranes in a treatment for proliferative vitreoretinal disorders includes an ophthalmic treatment tool for using in an ophthalmic surgery, the tool including: a grip portion; a rod-shaped body attached to one end of the grip portion; an elastic body fitted along a direction toward a front end of the rod-shaped body to the front end side of the rod-shaped body; and hard inorganic fine-grains or particles fixed on a tapered tip of the elastic body.

6 Claims, 4 Drawing Sheets

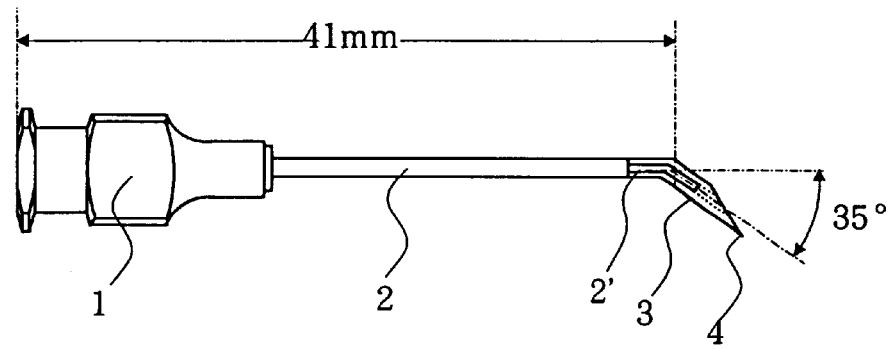
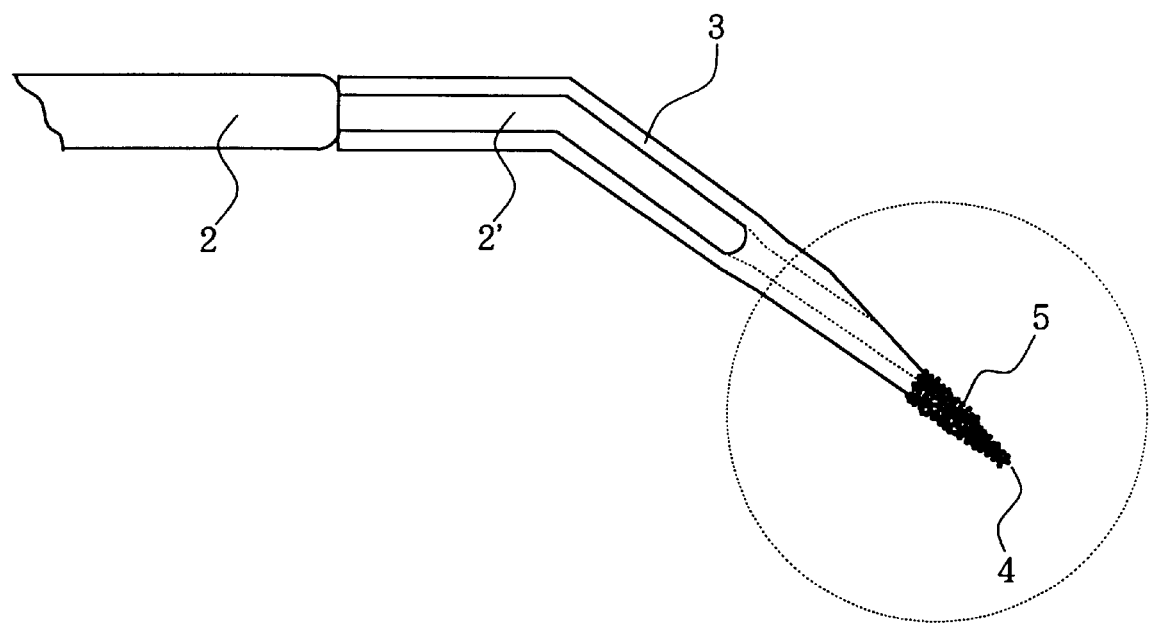

MEMBRANE ERASER

BACKGROUND OF THE INVENTION

1. Field of the Invention

The present invention relates to a membrane eraser (hereinafter, called an ophthalmic treatment tool) and, in more detail, to a new instrument which is useful for removing proliferative membranes in a treatment for proliferative vitreoretinal disorders.

2. Description of the Background

A continuing challenge to vitreoretinal surgeons is the separation of proliferative membranes from the neurosensory retina without injury or harm to the neurosensory retina in the treatment for proliferative vitreoretinal disorders. For such a treatment, the removal of proliferative membranes from the surface of the retina is required in a wide variety of pathologic conditions and surgical situations. Various intraocular picks and intraocular forceps have been previously used for the removal of proliferative membranes.

However, the way that proliferative membranes are removed by the above conventional instruments may carry the risk of causing damage to the retina at all times. Besides, there is a problem as follows. That is, "immature proliferative membranes" seen in proliferative vitreoretinal disorders may be friable, difficult to peel off as films, and often cannot be sufficiently removed from the surface of the retina, so that the unremoved or remaining proliferative membranes can be the source of subsequent reproliferation and thus the likelier it become that the reproliferative membranes again require the removal thereof as time elapses.

SUMMARY OF THE INVENTION

It is, therefore, an object of the invention to provide a new instrument which can solve the foregoing problems regarding the prior arts and can be useful for removing proliferative membranes in a treatment for proliferative vitreoretinal disorders.

This object is achieved by the present invention as follows: the invention is directed to an ophthalmic treatment tool for using in an ophthalmic surgery, which comprises: a grip portion; a rod-shaped body attached to one end of the grip portion; an elastic body fitted along a direction toward a front end of the rod-shaped body to the front end side of the rod- shaped body; and a plurality of hard inorganic fine-grains or particles fixed on a tapered front tip of the elastic body.

According to the ophthalmic treatment tool with the construction mentioned above, it is possible to more appropriately separate and remove proliferative membranes consisting of thin and delicate tissues from the retina while more remarkably reducing the risk of causing damage to the retina or of forming the retinal tear, in contradistinction to the case of the conventional instruments being used. Various other objects, features and attendant advantages of the present invention will be more fully appreciated as the same becomes better understood from the following detailed description when considered in connection with the accompanying drawings in which like reference characters designate like or corresponding parts throughout the several views and wherein:

BRIEF DESCRIPTION OF THE DRAWINGS

FIG. 1b is a partially enlarged view of the ophthalmic treatment tool in FIG. 1a;

FIG. 1c is a front view of a tip portion of the ophthalmic treatment tool in FIG. 1a;

FIG. 2a is a side view of an ophthalmic treatment tool of the other embodiment according to the present invention;

FIG. 2b is a partially enlarged view of the ophthalmic treatment tool in FIG. 2a; and FIG. 2c is a front view of a tip portion of the ophthalmic treatment tool in FIG. 2a.

DESCRIPTION OF THE PREFERRED EMBODIMENT

Figure 1A:
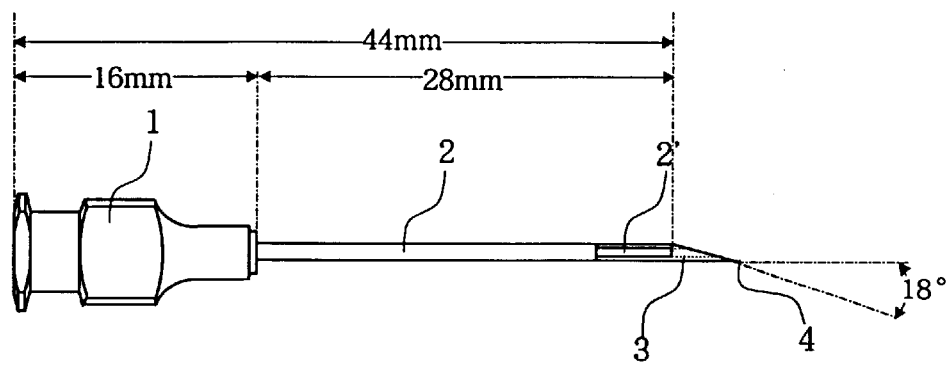
FIG. 1a is a side view of an ophthalmic treatment tool of one embodiment according to the present invention.

The invention will now be more specifically described with reference to embodied configurations illustrated in the drawings attached hereto, but the present invention should not be restricted to those embodied configurations.

Figure 1B:
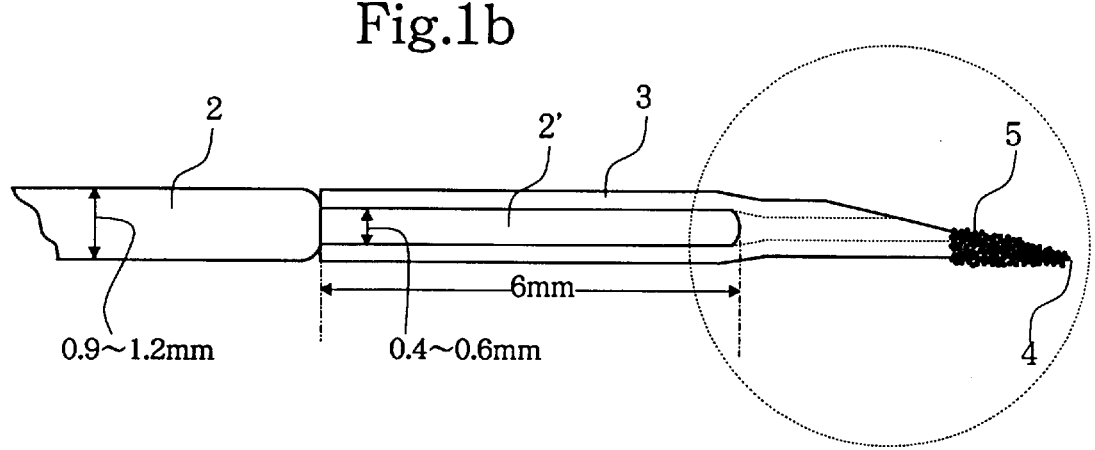
Figure 1C:
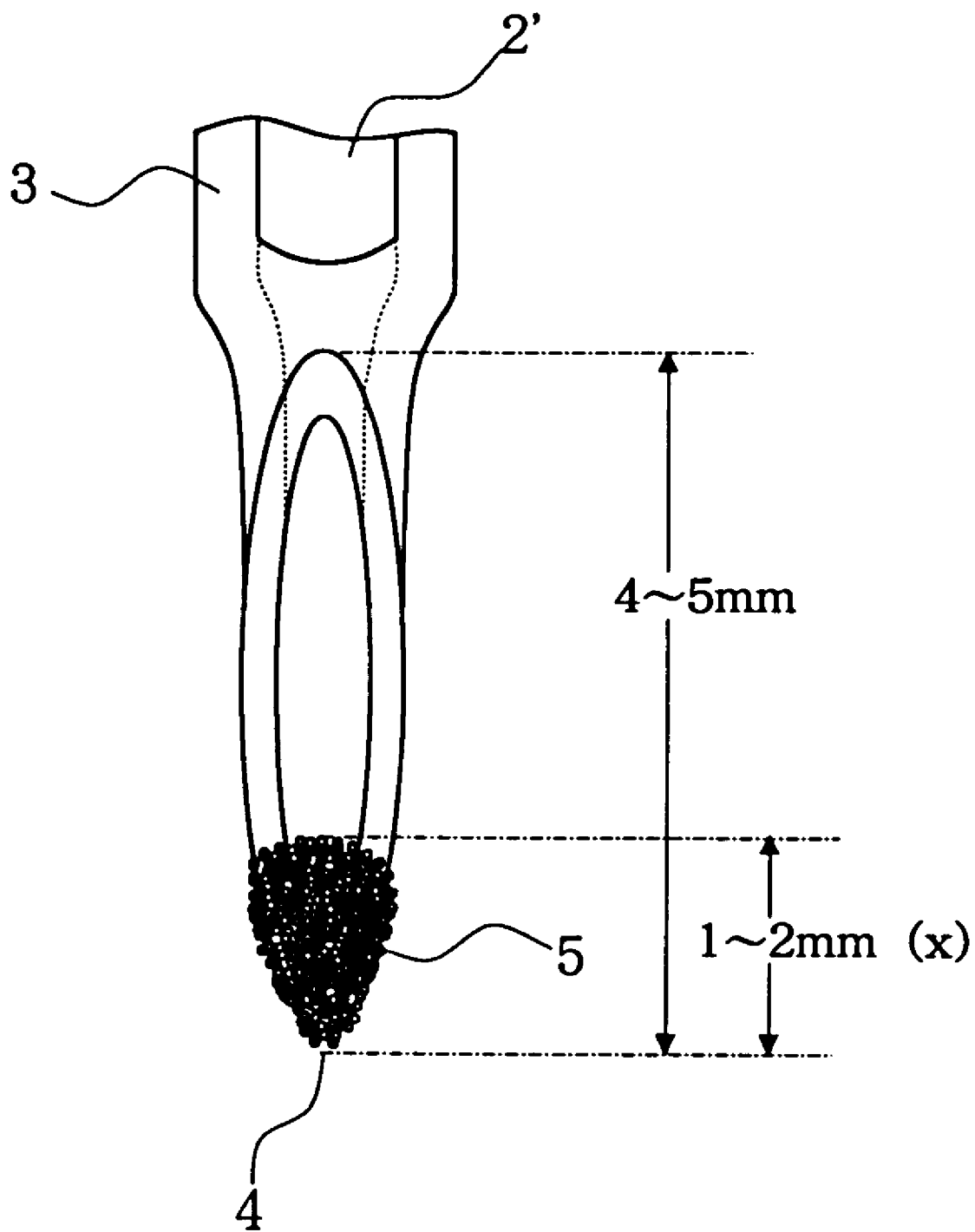
Figure 2C:
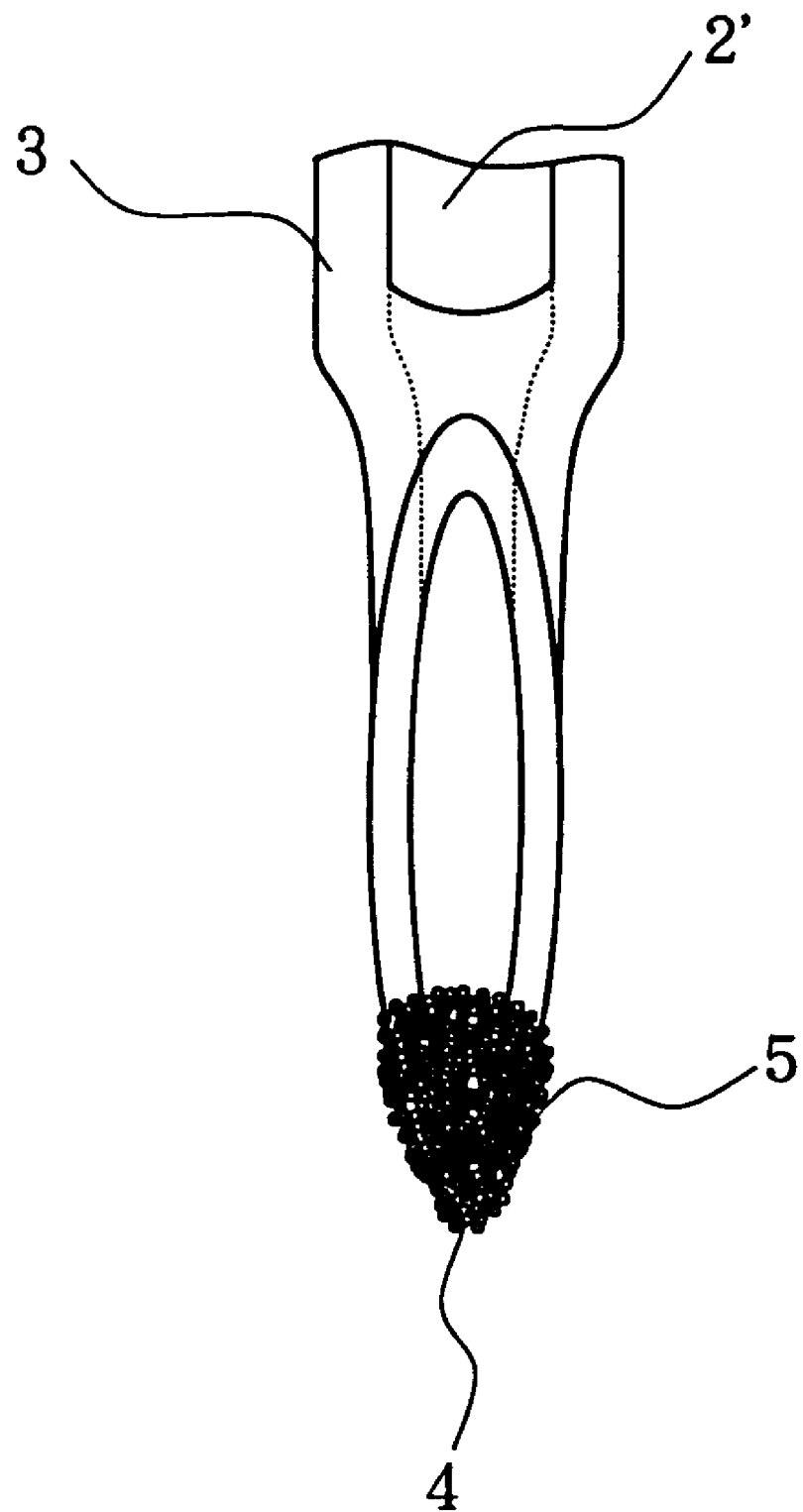

Referring to FIGS. 1a to 1c and FIGS. 2a to 2c, among those figures are FIG. 1a which is a side view of an ophthalmic treatment tool of one embodiment according to the present invention, FIG. 1b which is its partially enlarged detail, FIG. 1c which is a front view of a tip portion of the ophthalmic treatment tool, and FIGS. 2a to 2c which are views showing a configuration according to a modification of the tool shown in FIGS. 1a to 1c.

An ophthalmic treatment tool of the present invention, as shown in the figures, is characterized by having a grip 1, a rod-shaped body 2 attached to one end of the grip 1, an elastic body 3 fitted along a direction toward a front end of the rod-shaped body 2 to the front end side of the body 2, and a group of hard inorganic fine—grains 5 of particles fixed on a tapered tip 4 of the elastic body The grip 1 can be well grasped by user's fingers for a surgery, which is not restricted to the example shown in the figure and may have any shape unless it troubles the users in their operation. In the case of grasp by the fingers, the grip 1 is suitably formed to be mostly as thick as e.g., pencils, pens, or chopsticks which the users are generally used to handling. With respect to materials, the grip 1 is made from material which have no hygienic problem, the material being, for example, wood, metal, plastic or the like, the metal being preferably used for the grip, the better of metals being silver, stainless steel, titanium or the like, the titanium being preferably used for the grip in the light of the strength, lightweight and/or others.

One end of the grip portion 1 is fixed to a rod-shaped body 2 in a certain way that may be modified as needed. The rod-shaped body 2 is provided for purposes of supporting an elastic body 3 which is placed on the front end side of the rod-shaped body 2. Although the rod-shaped body 2 is made from any material which creates no problem in terms of of sanitation as is the case with the grip 1, the rod-shape body 2 is preferably made from titanium in common reason with the grip 1.

An end portion of the rod-shaped body 2 is provided with the elastic body 3. The elastic body 3 is translucent and takes the form of a tube, which is fixed to the rod-shaped body 2 by being inserted on an end 2' of the rod-shaped body. In a configuration shown in the figure, the rod-shaped body 2 is tapered in a part of the front end side thereof to form a slender line portion 2' of the rod-shaped body, and the slender line portion 2' is squeezed into the tube-shaped elastic body 3, whereby the bodies 2 and 3 are fixed to each other. The manner of coupling of both, however, should not be restricted to the configuration shown in the figure, to which any type of coupling can be applied, within tight coupling of the rod-shaped body and the elastic body thus resulting.

The elastic body 3 is made from any material which creates no sanitary problems in ophthalmic surgery as in the cases mentioned above, for example, the material of the elastic body 3 being natural rubber, synthetic rubber, polyurethane rubber, silicone rubber, fluorocarbon rubber, or the like, the elastic body being most suitably made from silicone rubber in the light of the pliability, inertness (sanitary property) and so on. The slender line portion 2' is not entirely inserted into a tube of the elastic body 3, whose front end side is thus not inserted on the slender line portion 2'. An elastic portion positioned on the figure's right side from the front end of the slender line portion 2' must be kept in a sufficiently pliable and flexible state so as not to carry the risk of causing damage to the retina and so on when peeling the membranes during the ophthalmic surgery.

The tip (in the figure, right end portion) of the elastic member 3 is formed in a tapered shape. The shape can be easily formed by cutting the tube-shaped elastic body 3 at a bevel. Although such cutting at a bevel causes a cross-sectional profile as in the case of a bamboo being cut at a bevel as shown in FIG. 1c, such a profile is not essential for the present invention. For instance, an elastic portion having no insertion of the slender line portion 2' may have no space. In this instance the tip of the elastic body 3 should be tapered only.

A great number of hard inorganic fine-grains 5 adheres around a tapered tip 4 of the elastic member 3, which have a function to peel and remove the proliferative membranes on the retina without injury to the retina. The hard inorganic fine-grains used hereon, should consist of any rigid fine-grains or particles which has chemical inertness and no problem in sanitation. For example, the fine-grains may be various kinds of fine-grains which are made of diamond, diamond-like carbon, ruby, sapphire, quartz, crystal, alumina, silica, silicon carbide, silicon nitride, marble, grindstone, or the like, and the grains 5 is most suitably made of diamond in the light of the chemical inertness and the hygiene and so on thereof.

The grains may range in size or diameter from 3 $\mu$m to 80 $\mu$m, preferably range between 9 and 30 $\mu$m. It has been found that proliferative membranes on the retina would not be sufficiently removed at any rate if the diameter of grains are out of the range.

A bonding between the fine-grains 5 and the elastic body 3 is preferably performed by using an suitable adhesive chosen in accordance with nature of the elastic member 3. If the elastic member is made from silicone rubber, a silicone base adhesive is preferably used. In addition to this, if an adhesive of two-liquid setting type, thermosetting type or photosetting type is used, the hard inorganic fine-grains are tightly fixed respectively after the adhesive constructs bridges and hardens as soon as the adhesive makes attachment, and then the adhesive becomes in chemical inertness to have no sanitary problem. The choices of an adhesive, of course, should not be restricted to the preferred examples mentioned above. A bonding of the hard inorganic fine-grains can be performed in any well-known way. However, it is desirable that the surfaces of the fine-grains are exposed externally, which are among the hard inorganic fine-grains bonded and fixed, are not covered with the adhesive. The bonding of the grains, namely, is desirably performed as follows: first, an appropriate adhesive is attached to the tip of the elastic member; secondly, the hard inorganic fine-grains are strewn on a surface of the attached adhesive to cover the surface; thirdly, a process that the adhesive constructs bridges and hardens is performed on condition that the fine-grains can be attached no more, to such an extent that a state of the rough surface of the attached group of fine-grains have activity in remove proliferative membranes. Following the completion of constructing bridges and hardening of the adhesive, it is preferable to remove fine-grains loosely attached to the tip of the elastic member (that is, fine-grains which may come off during an ophthalmic surgery) by performing an ultrasonic cleaning process and the like in advance.

Although FIG. 1c shows an example of a range that the hard inorganic fine-grains 5 are fixed to the tapered portion 4 of the elastic member 3, the example is merely one example. Such a range is not restricted to a particular range within keeping activity at removing proliferative membranes on a retina. The range (x), which has been obtained based on experiment and seems to be preferable, has a width between 0.5 and 3 mm substantially. The ophthalmic treatment tool according to the present invention is realized as mentioned above. It should be noted that some measurements inscribed in the figures do not limit the present invention but are to easily understand the invention. Further note that FIG. 2 shows an ophthalmic treatment tool of the other embodiment according to the present invention.

The inventors have used the treatment tool shown in the figures for a series of their patients who have undergone an operation of vitreous removal at their macular hole, and the tool has been applied to a retinal surface around a macular hole after peeling the rear vitreous. Furthermore, the treatment tool shown in the figures has been applied for treatment of the proliferative vitreoretinal disorders with the purpose of removing immature proliferative membranes and pigmented cells from a surface of the retina.

In further detail, the inventors have used the treatment tool shown in the figures for eyes of seven patients which show the macular holes (Gass stages II, III and IV), and as a result, it has been able to successfully close the macular holes in all eyes. In three cases of proliferative vitreoretinal disorders, thin friable proliferative membranes were removed effectively. The inventors did not encounter any complications during their experience with the treatment tool shown in the figures. Neither retinal hemorrhages nor retinal tears have occurred, although the treatment tool shown in the figures are possible with injudicious use.

During the development of the treatment tool according to the present invention, hard inorganic fine-grains (e. g., diamond particles) were occasionally shed onto the retinal surface. However, any shed particles could easily be aspirated and removed by an extrusion needle, and any retained inert diamond particles are unlikely to cause retinal damage or toxicity. The inventors were successful in minimizing the shedding of particles under surgery by introducing a step of sonication cleaning process to previously remove the grains loosely adhering to the tip portion of the elastic body during manufacturing. Currently rarely if ever, has there been observed shedding of the hard inorganic fine-grains.

The roughened surface of the elastic body which is an extreme tip of the treatment tool according to the invention, the roughened surface being due to existing fine- grains, allows the proliferative membranes to be removed without the application of high degrees of force on the retina in the removal of the proliferative membranes.

The treatment instrument embodying the present invention differs from rigid instruments such as picks and forceps applying mechanical force to the synechia portion between the proliferative membranes and the retina, whose slender profile and flexibility of the front tip increases visualization of the area of interest in an ocular tissue during a surgery and enables the treatment to be performed properly and easily.

Since the front tip of the tool covered with the hard inorganic particles scours the proliferative membranes, the proliferative membranes can be seen to separate from the surface of the retina. Even if a proliferative membranes to be removed is remarkably thin, therefore, changes in the light reflex, color, and the other detail tell the surgeon which regions of the proliferative membrane have been separated, the surgeon being able to perfectly perform the treatment.

In the present tool according to the invention, the mechanism as mentioned above makes the tool especially useful for the removal of residual cortical vitreous proliferative membranes or retinal interfaces from the surrounding area of a macular hole. The tool is also effective for removing "immature" proliferative membranes and removing pigmented cells from the surface of the retina, which, if left behind, can be a nidus for future membrane formation. Hence, the present tool may markedly increase the likelihood of success of the ophthalmic surgery.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A membrane eraser used for ophthalmic surgery, comprising:

a grip portion;

a rod shaped body attached to one end of said grip portion;

an elastic body fitted along a direction toward a front end of said rod-shaped body to the front end side thereof and having a hollow tapered front tip; and a plurality of hard, inorganic fine-grains fixed on said tapered front tip of said elastic body wherein said grains are located in a range of 0.5 mm to 3.0 mm from an end portion of said front tip for removal of membrane tissue on a retina of an individual.

2. A membrane eraser according to claim 1, wherein said elastic body comprises silicone rubber.

3. A membrane eraser according to claim 1, wherein said hard inorganic fine-grains comprise grains having a range in diameter from 3 to 80 $\mu$m.

4. A membrane eraser according to claim 1, wherein said hard inorganic fine-grains comprise diamond particles.

5. A membrane eraser according to claim 1, wherein said rod-shaped body comprises titanium.

6. A membrane eraser according to claim 1, wherein said hard inorganic fine-grains are fixed by a silicone base adhesive to said front tip.

* * * * *